US008852241B2

(12) United States Patent
Datta

(10) Patent No.: US 8,852,241 B2
(45) Date of Patent: Oct. 7, 2014

(54) SURGICAL DEVICES AND METHODS PROVIDING SACROILIAC STABILIZATION

(76) Inventor: Devin Datta, Melbourne, FL (US)

( * ) Notice: Subject to any disclaimer, the term of this patent is extended or adjusted under 35 U.S.C. 154(b) by 69 days.

(21) Appl. No.: 13/565,975

(22) Filed: Aug. 3, 2012

(65) Prior Publication Data
US 2013/0035727 A1 Feb. 7, 2013

Related U.S. Application Data

(60) Provisional application No. 61/515,075, filed on Aug. 4, 2011.

(51) Int. Cl.
| A61B 17/88 | (2006.01) |
| A61B 17/17 | (2006.01) |
| A61B 17/70 | (2006.01) |
| A61B 17/16 | (2006.01) |
| A61B 17/86 | (2006.01) |

(52) U.S. Cl.
CPC ......... *A61B 17/1671* (2013.01); *A61B 17/7032* (2013.01); *A61B 17/1757* (2013.01); *A61B 17/1631* (2013.01); *A61B 17/864* (2013.01); *A61B 2017/1602* (2013.01); *A61B 17/7055* (2013.01)
USPC .............................. 606/279; 606/86; 606/246

(58) Field of Classification Search
CPC ................................ A61B 17/88; A61B 17/70
USPC ............................................ 606/246, 86, 279
See application file for complete search history.

(56) References Cited

U.S. PATENT DOCUMENTS

| 5,098,434 | A | * | 3/1992 | Serbousek | 606/308 |
| 5,108,397 | A | * | 4/1992 | White | 606/60 |
| 5,593,407 | A | * | 1/1997 | Reis | 606/261 |
| 5,725,596 | A | * | 3/1998 | Burke | 623/23.21 |
| 5,800,435 | A | | 9/1998 | Errico | |
| 7,763,053 | B2 | * | 7/2010 | Gordon | 606/258 |
| 8,128,666 | B2 | | 3/2012 | Falahee | |
| 2004/0039383 | A1 | | 2/2004 | Jackson | |
| 2004/0193157 | A1 | | 9/2004 | Falahee | |
| 2006/0047282 | A1 | * | 3/2006 | Gordon | 606/61 |
| 2008/0306552 | A1 | | 12/2008 | Winslow | |
| 2010/0042149 | A1 | * | 2/2010 | Chao et al. | 606/246 |
| 2010/0094290 | A1 | * | 4/2010 | Vaidya | 606/60 |
| 2010/0160981 | A1 | * | 6/2010 | Butler et al. | 606/308 |
| 2012/0296428 | A1 | * | 11/2012 | Donner | 623/17.11 |

* cited by examiner

*Primary Examiner* — Eduardo C Robert
*Assistant Examiner* — Tessa Matthews
(74) *Attorney, Agent, or Firm* — Allen, Dyer, Doppelt, Milbrath & Gilchrist, P.A.

(57) ABSTRACT

A surgical method is for at least one ilium having an iliac crest and inner and outer tables on opposing sides of the iliac crest. The method may include inserting at least one base into the ilium, where the at least one base has a channel therein. The method may further include inserting a support member through the ilium and through the channel of the at least one base so that the support member extends between the inner and outer tables, and securing the support member to the at least one base.

20 Claims, 11 Drawing Sheets

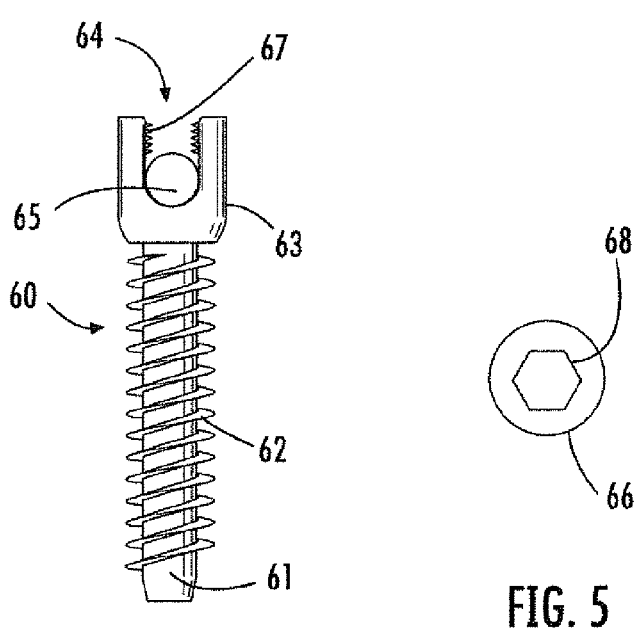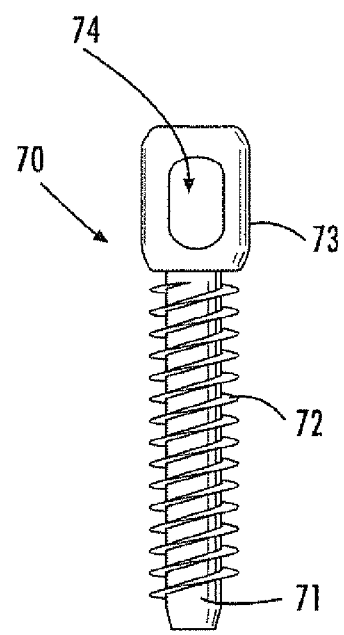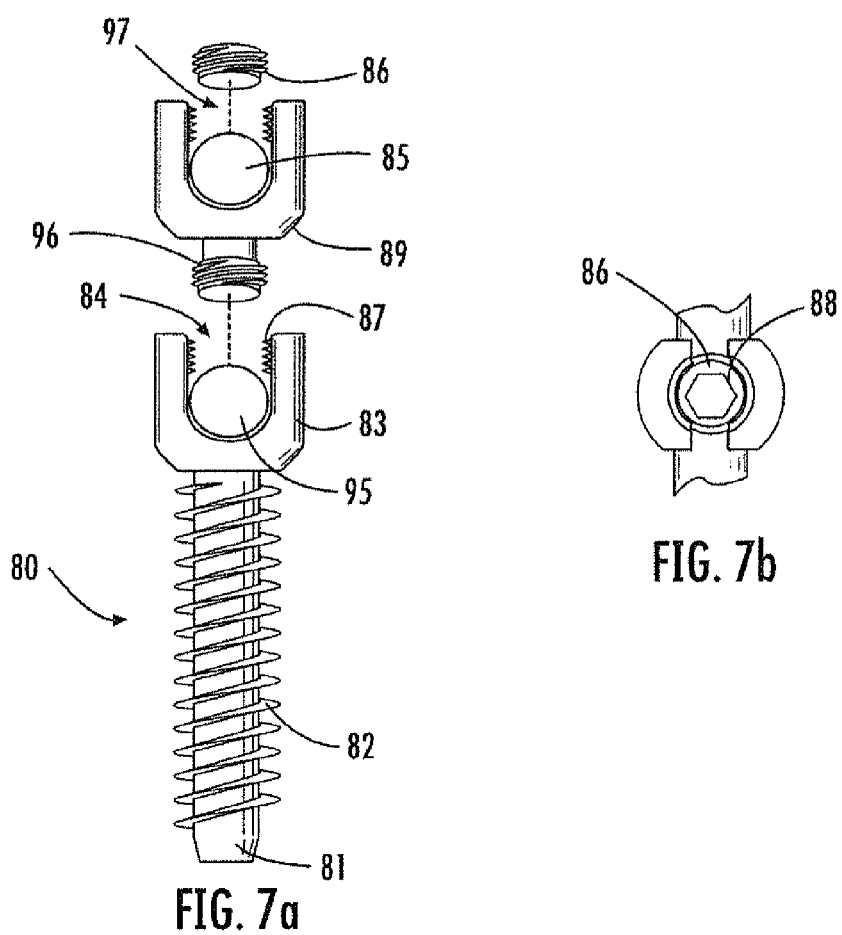

SURGICAL DEVICES AND METHODS PROVIDING SACROILIAC STABILIZATION

CROSS-REFERENCE TO RELATED APPLICATIONS

The present application claims the benefit of U.S. provisional app. No. 61/515,075, filed Aug. 4, 2011, which is hereby incorporated herein in its entirety by reference.

FIELD OF THE INVENTION

The present invention relates to the field of surgical procedures, and, more particularly, to musculoskeletal surgical procedures and associated devices.

BACKGROUND OF THE INVENTION

The sacroiliac joint (SI joint) is increasingly being diagnosed as a common pain generator. That is, SI joint degenerative disease and instability are being diagnosed and treated more commonly. Contributing factors include post traumatic injury, accelerated wear/instability after lumbar fusion, post pregnancy pain/instability and longer life span combined with a more active lifestyle in many patients. In addition, complex spine surgeries, such as for correction of sagittal plane deformity, often require iliac fixation to maintain correction in patients with a high pelvic incidence or high risk of lumbo-sacral hardware failure.

High energy pelvic ring injuries that involve disruption of the SI joint and/or displaced fractures of the sacrum present unique challenges to the orthopedic traumatologist. Some sacral fractures require solid posterior stabilization, which may be difficult to achieve with typical treatment methods. Furthermore, vertically unstable sacral fractures/SI joint disruptions have a relatively high incidence of neurovascular injury and may require unique stabilization. Typically, a spinal surgeon will be involved to perform lumbo-pelvic stabilization of these injuries to provide vertical stability of the injury. However, there may be significant soft tissue trauma associated with these injuries, making extensive surgical approaches of elevated risk in terms of infection and wound complications.

Current techniques and instrumentation systems may require extensive surgical exposure and dissection. Moreover, such instrumentation systems are typically designed for other applications, and not to connect and stabilize the lumbar spine and pelvis. As a result, this can make the surgical times longer and more frustrating for surgeons and surgical staff. For example, traditional posterior iliac screws are often prominent because the posterior iliac crest is relatively subcutaneous. Yet, this sometimes makes hardware painful for the patient and at risk for pressure soreness following surgery.

SUMMARY OF THE INVENTION

It is therefore an object of the present invention to provide enhanced methods and devices for stabilization of the spine and/or pelvis.

This and other objects, features, and advantages are provided by a surgical method for at least one ilium having an iliac crest and inner and outer tables on opposing sides of the iliac crest. The method may include inserting at least one base into the ilium, where the at least one base has a channel therein. The method may further include inserting a support member through the ilium and through the channel of the at least one base so that the support member extends between the inner and outer tables, and securing the support member to the at least one base. Accordingly, the method may allow for relatively shorter surgical times, and help reduce a likelihood of pressure soreness to the patient from protruding hardware, for example.

More particularly, the support member may comprise a rod, for example. Furthermore, in some embodiments the at least one ilium may comprise a left ilium and a right ilium. In such example embodiments, inserting the at least one base may comprise inserting a first base in the left ilium and a second base in the right ilium. Further, inserting the support member may comprise inserting a proximal end of the support member through the left ilium and the first channel of the first base so that the proximal end extends between the inner and outer tables of the left ilium, and inserting a distal end of the support member through the right ilium and the second channel of the second base so that the distal end extends between the inner and outer tables of the right ilium. Moreover, securing may comprise securing the support member to the first base and the second base.

In another example embodiment, inserting the support member may comprise inserting a proximal end of the support member through the ilium and through the channel of the at least one base, and the method may further include coupling a distal end of the support member to an adjacent vertebral body. Moreover, coupling the distal end of the support member to the adjacent vertebral body may comprise coupling the distal end to a spinal rod also coupled to the adjacent vertebral body.

Additionally, coupling the distal end of the support member to the adjacent vertebral body may comprise coupling the distal end to a bone screw device carried by the adjacent vertebral body. More particularly, the bone screw device may include a threaded base configured to be screwed into the vertebral body, and a first head carried by the threaded based and defining a first channel therein, where the first channel is configured to receive a support rod and the first head has first internal threads within the first channel. The bone screw device may further include a second head comprising a threaded base configured to be threadably coupled with the first inner threads to secure the support rod within the first channel of the first screw head, and an articulating head portion coupled to the threaded base and defining a second channel therein, where the articulating head is configured for polyaxial movement relative to the threaded base. Accordingly, coupling the distal end of the support member to the adjacent vertebral body may further comprise coupling the distal end of the support member within the second channel of the articulating head portion.

By way of example, inserting the at least one base into the ilium may comprise inserting the at least one base into the ilium through the iliac crest. Furthermore, the at least one base may have a threaded exterior, and inserting the at least one base into the ilium may comprise screwing the at least one base into the ilium through the iliac crest. Additionally, inserting the base into the ilium may further comprise recessing the base within the ilium so that the base is flush with or below a surface of the iliac crest.

The at least one base may comprise an articulating head defining the channel therein. The articulating head may have a threaded interior, and securing the support member may further comprise threadably fastening a set screw to the interior threads of the articulating head.

A related bone screw device may include a threaded base configured to be screwed into a bone, and a first head carried by the threaded based and defining a first channel therein. The first channel may be configured to receive a first support rod, and the first head may have first internal threads within the first channel. The bone screw device may further include a second head comprising a threaded base configured to be threadably coupled with the first inner threads to secure the first support rod within the first channel of the first screw head, and an articulating head portion coupled to the threaded base and defining a second channel therein configured to receive a second support rod. The articulating head may be configured for polyaxial movement relative to the threaded base.

More particularly, the articulating head portion may have second internal threads within the second channel, and the bone screw device may further include a set screw configured to be threadably coupled with the second internal threads to secure the second support rod within the second channel. The articulating head portion may further have external threads on an outer surface thereof which are reversed with respect to the second internal threads. Additionally, the first head may be configured for polyaxial movement with respect to the threaded base.

BRIEF DESCRIPTION OF THE DRAWINGS

FIGS. 4 and 5 are side and top views, respectively, of an example bone screw and associated set screw which may be used with one or more of the methods of FIGS. 1-3.

FIG. 6 is a side view of an alternative embodiment of the bone screw of FIG. 4.

FIGS. 7a and 7b are, respectively, side and top views of another example bone screw device and associated articulating head assembly, which may provide a set screw for a spinal rod and also a holder for an iliac support member, and which may be used with one or more of the methods of FIGS. 1-3.

DETAILED DESCRIPTION OF EXAMPLE EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements or steps in different embodiments.

Figure 1:
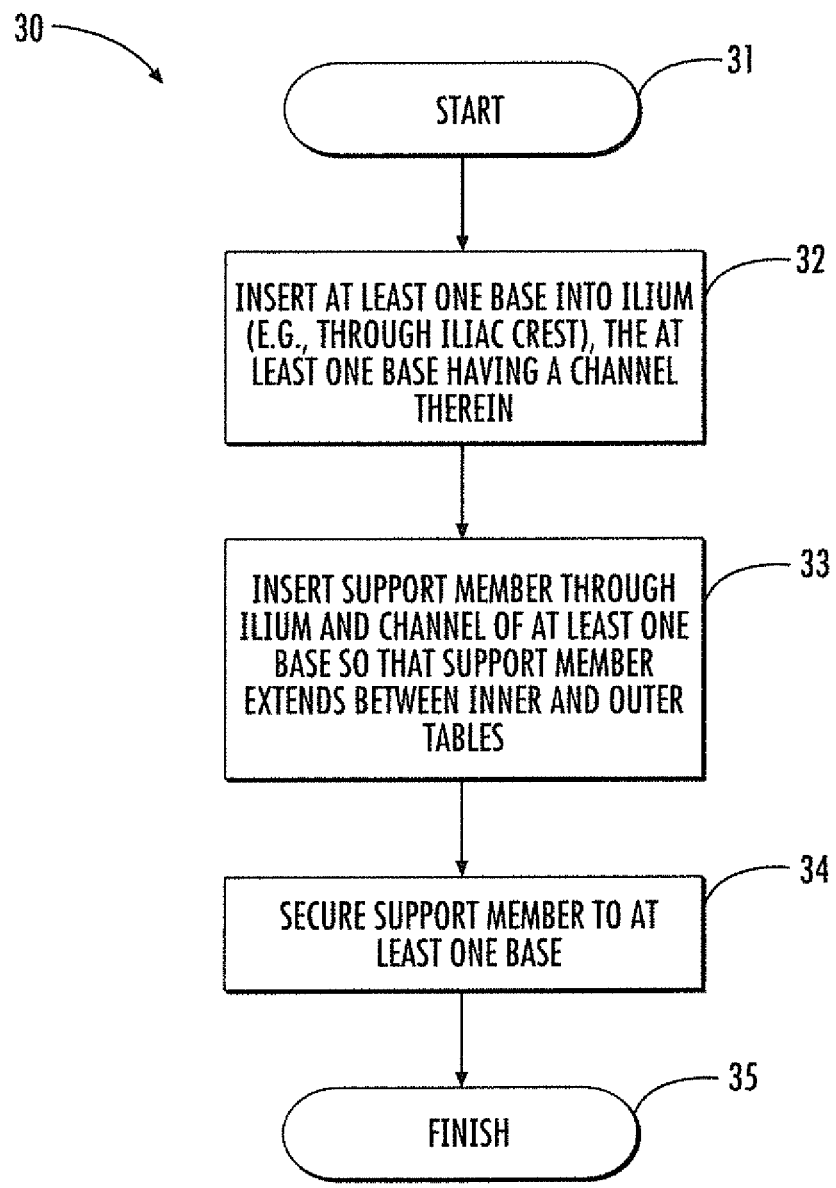
FIGS. 1-3 are flow diagrams illustrating various surgical method aspects of lumbo-pelvic and/or trans-iliac stabilization in accordance with the invention.
Figure 14:
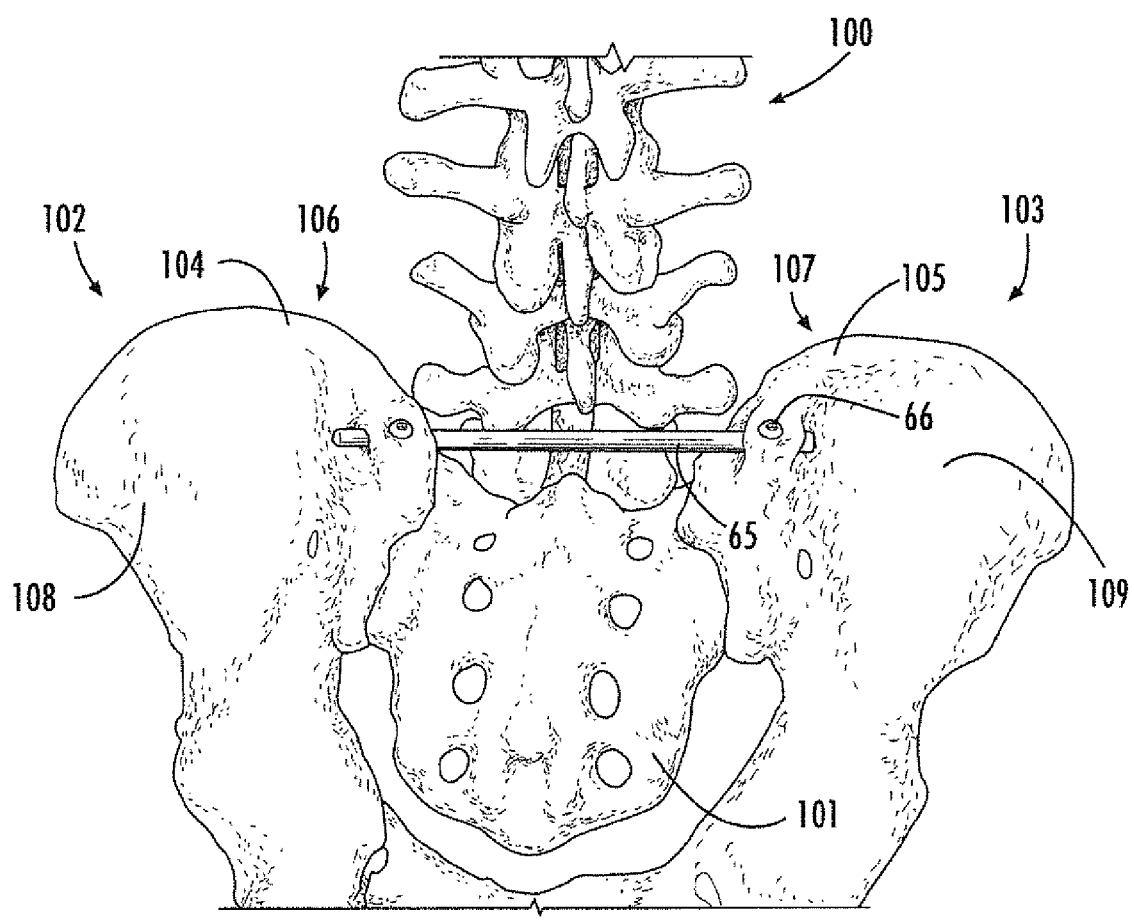
FIG. 14 is a posterior view of a lumbar spine and pelvis illustrating an example trans-iliac stabilization configuration in accordance with the invention.

Referring initially to the flow diagram 30 of FIG. 1 and FIGS. 4 and 14, a surgical method and associated devices which may advantageously be used to provide stability to portions of a patient's lower back, including the lumbar spine 100, sacrum 101, and/or ilia (e.g., a left ilium 102 and a right ilium 103), are first described. Each ilium 102, 103 has a respective iliac crest 104, 105. The left ilium 102 has an inner table or surface 106 and an outer table or surface 108 on opposing sides of the iliac crest 104. Similarly, the right ilium 103 has an inner table or surface 107 and an outer table or surface 109 on opposing sides of the iliac crest 105.

Generally speaking, the methods and associated devices described herein may be used to perform various pelvic and/or lumbo-pelvic fusions or stabilization procedures. Beginning at Block 30, one or more bases 60 are inserted into one or both of the ilia 102, 103, at Block 32. In the illustrated example, the base 60 is a bone screw having a shaft 61 with threads 62 to be screwed into the given ilium 102, 103 (or into portions of the lumbar spine 100 or sacrum 101, as will be described further below), although other types of bases and attachment arrangements besides threads may be used in different embodiments. The tip of the shaft 61 may be blunt to prevent violation of the iliac inner/outer bone tables 104, 105 in some embodiments.

The bone screw 60 may be inserted into a given ilium 102, 103 through the respective iliac crest 104, 105 thereof. The bone screw 60 further includes a head 63 thereon which defines a channel 64 therein into which a support member 65 is inserted, at Block 33. The head 63 may be an articulating head that is rotatable and/or capable of being pivoted to provide movement or articulation along multiple axes (i.e., a polyaxial head) to facilitate alignment with the support member 65 in some embodiments. For example, the head 63 may have a ball-and-socket joint, etc. By way of example, the screw 60 may have a diameter of about 6.5 mm to about 9.5 mm, and a length of about 50 mm to about 90 mm (including the head 63), although other dimensions may be used in different embodiments.

In the illustrated example, the support member 65 is a stabilization rod, which may be a rigid (or semi-rigid) rod made of surgical grade material (e.g., stainless steel, etc.). However, in other embodiments different support members 65 besides rods may be used, such as elastic bands, cables, etc. In this regard, the channel(s) 64 need not always be centered within the screw head 63, but instead may take the form of groves, slots or recesses on an exterior surface(s) which may be used to facilitate attachment of the support member 65, for example. A rod may be curved with a threaded end that may be used to attach to a screwdriver/guide in some embodiments. A double-threaded straight rod may be used in some embodiments for trans-iliac fixation to allow compression between the iliac crests 104, 105. A washer/nut (not shown) may be applied to the distal end of the straight rod or to both ends of the straight rod flush with the iliac crest for additional stability, if desired. However, threaded rods need not be used in all embodiments.

In particular, the support member 65 is inserted through a given ilium 102, 103 through the channel 64 of the bone screw 60 so that the support member extends between the respective inner and outer tables 106, 108 or 107, 109, as seen in FIG. 14. In the illustrated example, a respective bone screw 60 is inserted into each ilium 102, 103 through the respective iliac crests 104, 105 thereof, and the support member 65 is secured within the channels 64 of each bone screw, at Block 34, which illustratively concludes the method of FIG. 1 (Block 35). More particularly, a set screw 66 may be screwed into inner threads 67 to secure the support member 65 within the channel 64 (see FIG. 5). In the present example, the set screw 66 has a hex head slot 68 for a hex head driver tool, although other suitable configurations may also be used.

An alternative bone screw 70 is shown in FIG. 6, which similarly includes a shaft 71 with threads 72 thereon, and a head 73 is carried on the top of the shaft. Here again, the head 73 has a channel 74 therein for receiving a support member (not shown in FIG. 6). However, the head 73 is enclosed at the top, as opposed to the "U" shaped head 63 of FIG. 4 which is open at the top.

Figure 15:
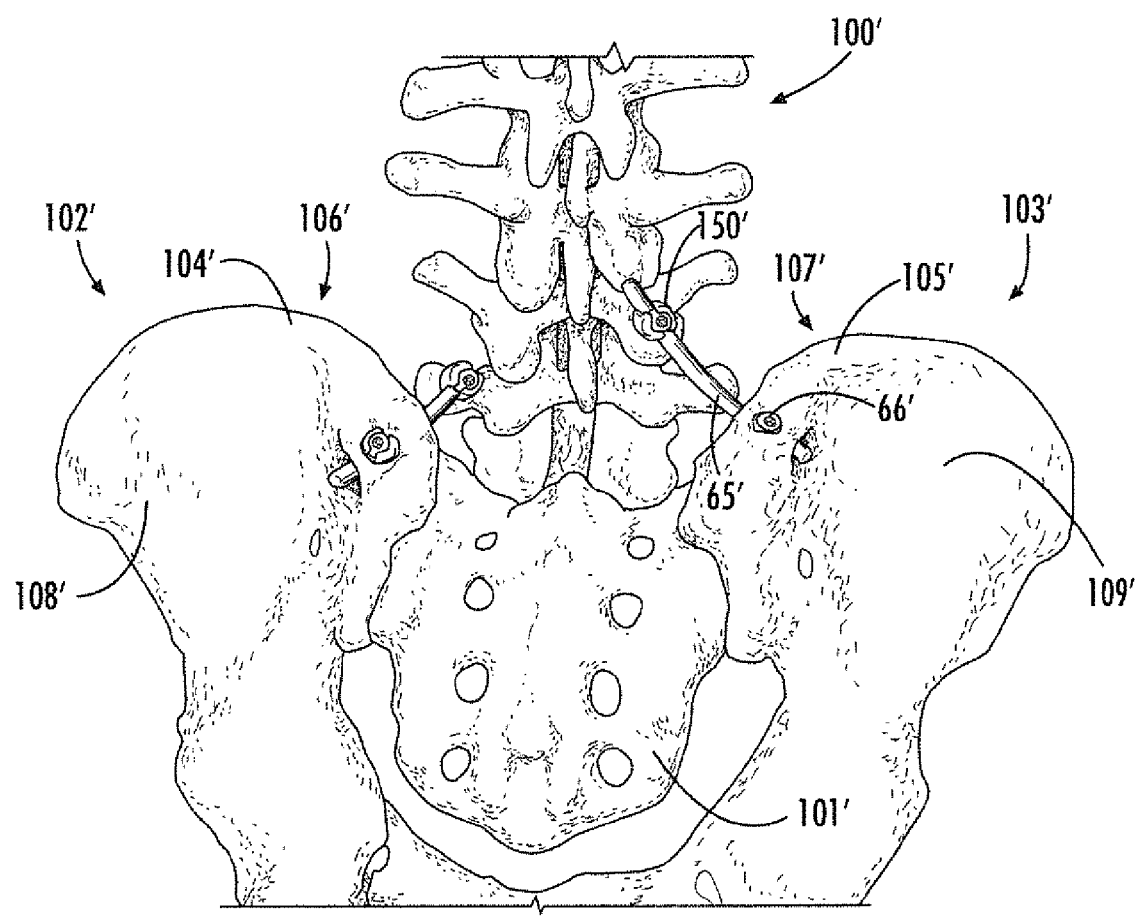
FIG. 15 is a posterior view of a lumbar spine and pelvis illustrating an example lumbo-pelvic stabilization configuration in accordance with the invention.
Figure 16:
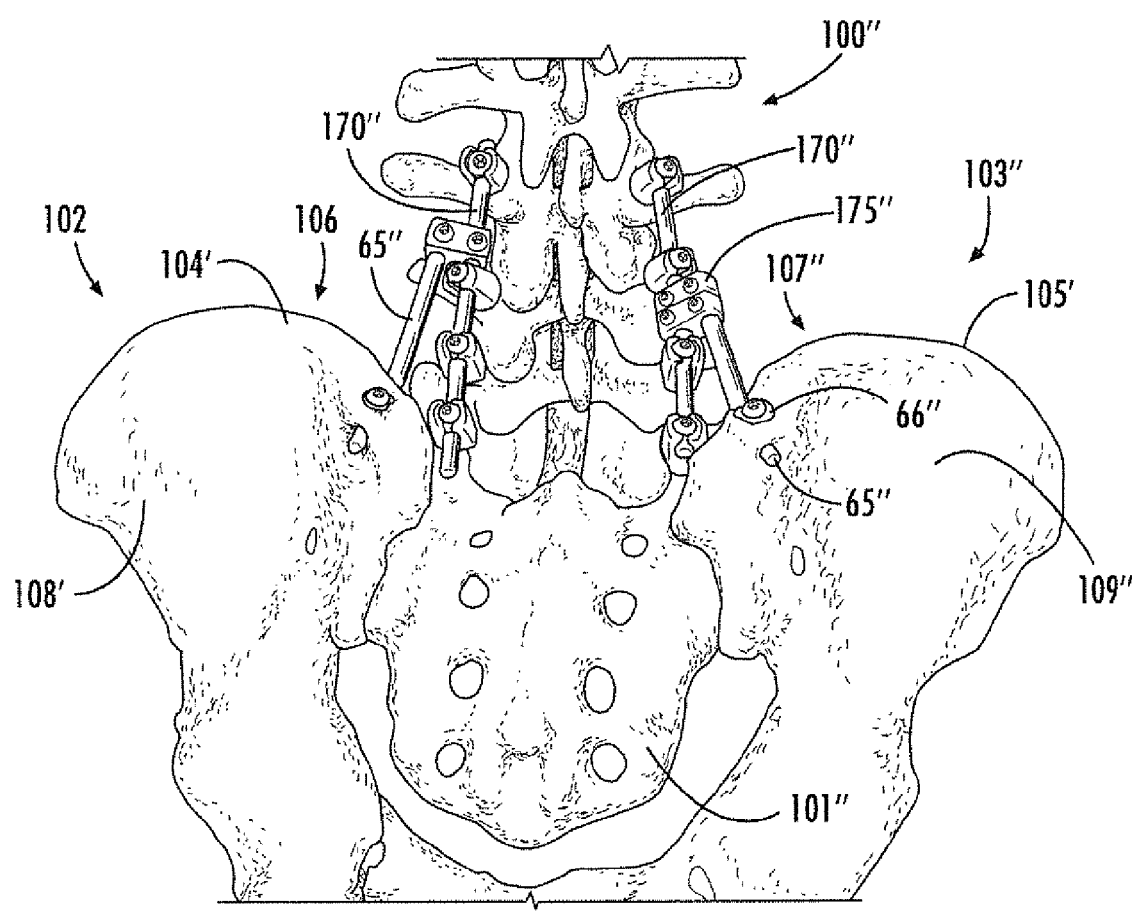
FIG. 16 is a posterior view of a lumbar spine and pelvis illustrating another example lumbo-pelvic stabilization configuration in accordance with the invention.
Figure 17:
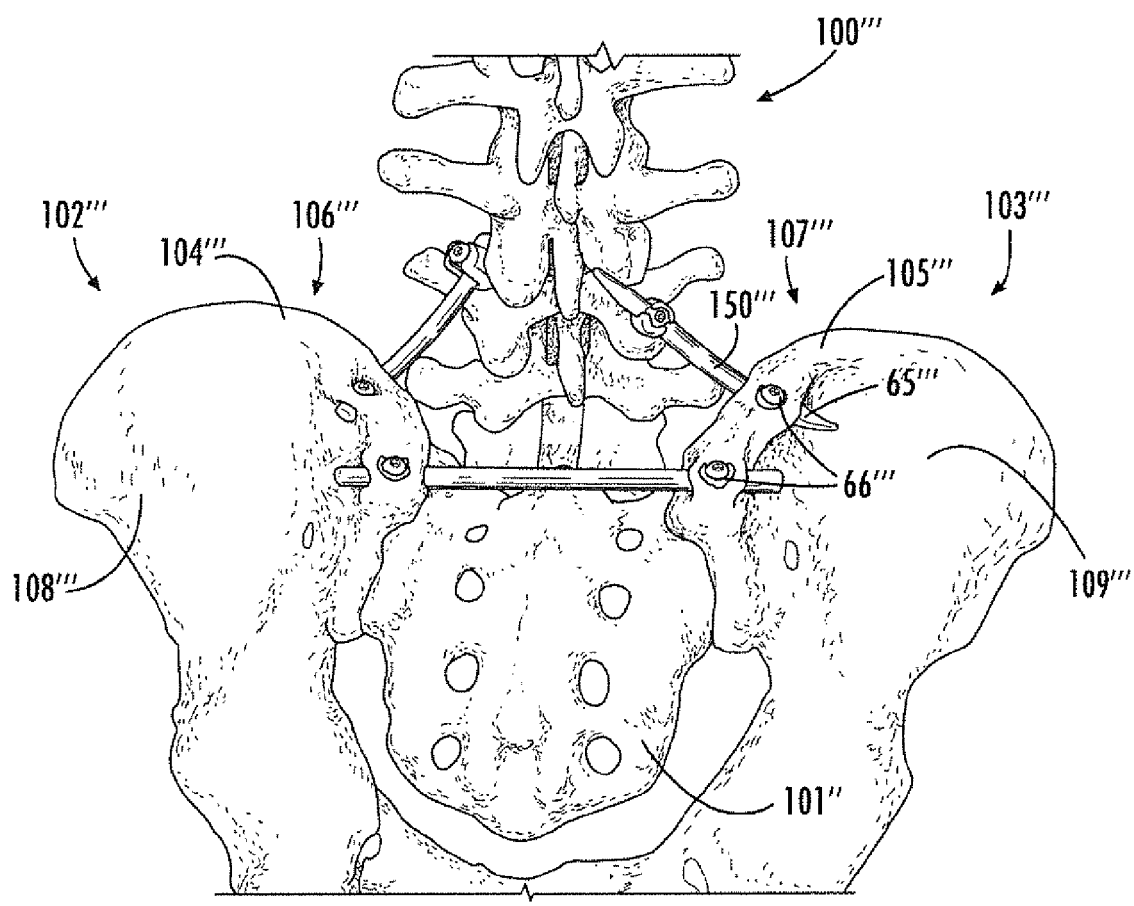
FIG. 17 is a posterior view of a lumbar spine and pelvis illustrating an example combination trans-iliac and lumbo-pelvic stabilization configuration in accordance with the invention.

Using the above-described approach, pelvic and/or lumbo-pelvic stabilization may be achieved using a mini-open percutaneous technique to apply and connect the bone screws 60 from one or both of the left ilium 102 and the right ilium 103 to the lumbar spine 100, and/or to one another (i.e., a trans-iliac fixation). A trans-iliac fixation is shown in FIG. 14, lumbo-pelvic fixation configurations are shown in FIGS. 15 and 16, and a combination trans-iliac and lumbo-pelvic fixation is shown in FIG. 17, which will be discussed further below. The heads 63 of the bone screws 60 may advantageously be recessed beneath the surface of the respective iliac crests 104, 105, which provides for little or no hardware prominence of the bone screws, as shown in FIG. 14.

Figure 3:
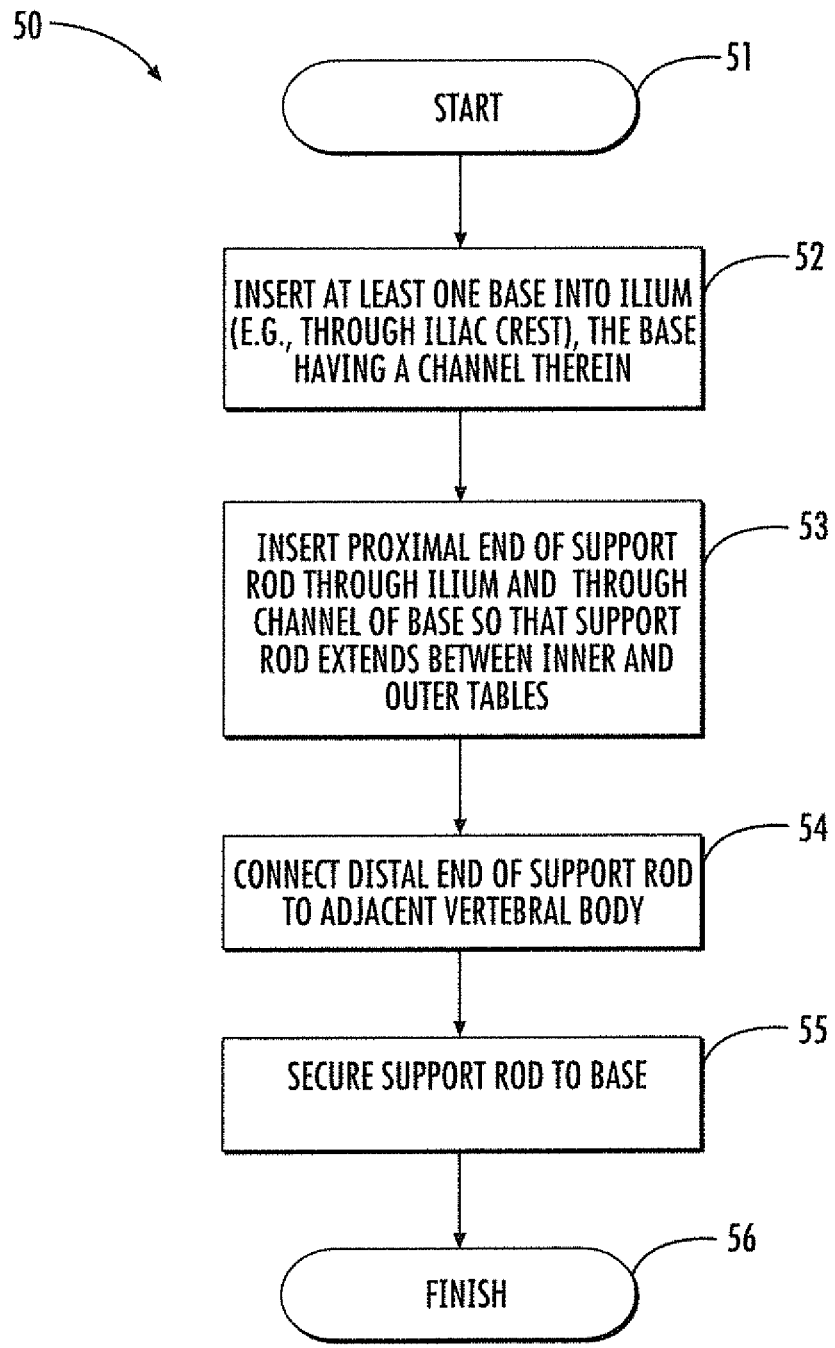

Referring to the flow diagram 50 of FIG. 3 and FIG. 15, a lumbo-pelvic stabilization configurations and associated steps are now described. Beginning at Block 51, an approximately three to six centimeter incision may be centered over the portion of the iliac crest 104', 105' where bone screw 60 placement is desired. If SI joint fusion is desired for the particular patient, the incision may be made be slightly medial to the iliac crest 104', 105' so that the extra-articular SI joint and iliac crest may both be accessed. By way of example, a high speed burr or an awl may be used to create a small opening between the inner and outer tables 106', 108' or 107', 109' of the respective iliac crests 104', 105'. Furthermore, a standard gear shift pedicle finder may be used, for example, to cannulate the trajectory desired while staying between the inner and outer tables 106', 108' or 107', 109' of the respective iliac crests 104', 105', which can be confirmed by a C-arm X-ray machine, for example, if desired.

Figure 8:
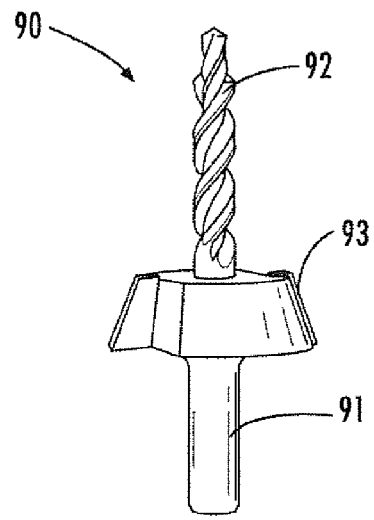
FIG. 8 is a side view of a drill bit which may be used for installation of the bone screws of FIGS. 4a, 5, and 6.

A screw router may then be used to ream an opening large enough through the given iliac crest 104', 105' to accommodate the iliac screw head so that it can be buried or recessed in the left ilium 102' or right ilium 103' to be flush or below the surface of the given iliac crest, as noted above (Block 52). In this regard, an iliac screw router bit 90 may be used, which illustratively includes a shank 91, a drill tip 92, and a router bit head 93 (see FIG. 8). The router bit 90 is configured to maintain a desired screw trajectory while creating room to completely bury the iliac screw head beneath the surfaces of the iliac crests 104', 105', an optionally allowing multiple degrees of movement in the case of a polyaxial head. This mobility makes aligning the construct easier for the surgeon. The drill tip 92 may also have a blunt end, if desired.

The surgeon may then connect or attach a distal end of the support member 65' to the lumbar spine 100' (or connect the support member 65" to an existing lumbar rod or construct 170" in the example of FIG. 16), and connect a proximal end of the support member to the iliac screw head, at Blocks 53-54. If there is no previous lumbar rod 170" available, then a percutaneous pedicle screw 150' may be used, e.g., at L14 or L15, as seen in FIG. 15. With use of a C-arm, Jamshidi trocar, and/or guide wire, tap and placement of the pedicle screw 150' may be performed using the percutaneous pedicle screw set, as will be appreciated by those skilled in the art. The support member 65' may be secured in place using set screws, etc., as described above, at Block 55, which concludes the method illustrated in FIG. 3 (Block 56).

One example lumbar or pedicle screw arrangement which provides enhanced connection capabilities for connecting to an iliac support member 85 is now described with reference to FIGS. 7a and 7b. A lumbar screw base 80 includes a shaft 82 with threads 82 thereon. A head 83 is carried on top of the shaft 81 opposite the tip. The head 83 may be a polyaxial head as described above in some embodiments, although a fixed head may also be used. The head 83 defines a channel 84, in which a spinal stabilization (e.g., lumbar) rod 95 is carried. Another polyaxial head 89 has a threaded base 96 which screws into the internal threads 87 of the head 83 to securely fasten the spinal rod 95 within the channel 84. The iliac support member 85 may then be placed within the channel 97 defined by the head 89 and secured in place by a set screw 86 having a hex head receiving slot 88, as similarly described above with reference to FIG. 5. It should be noted that the screw base 80 and head 83 may also be used as an iliac screw, e.g., by screwing the set screw 86 directly into the internal threads 87 and omitting the head 89.

Figure 12:
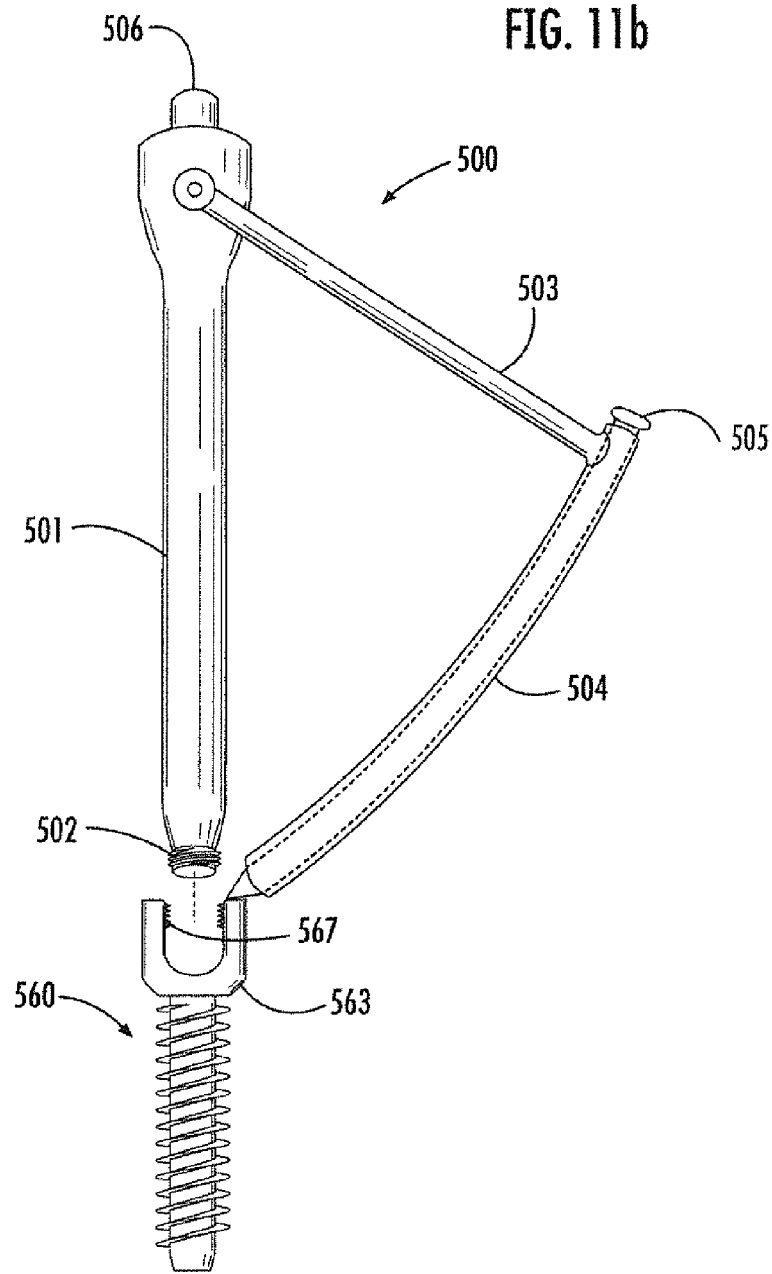
FIG. 12 is a side view of an iliac drill guide system which may be used with one or more of the methods of FIGS. 1-3.
Figure 13:
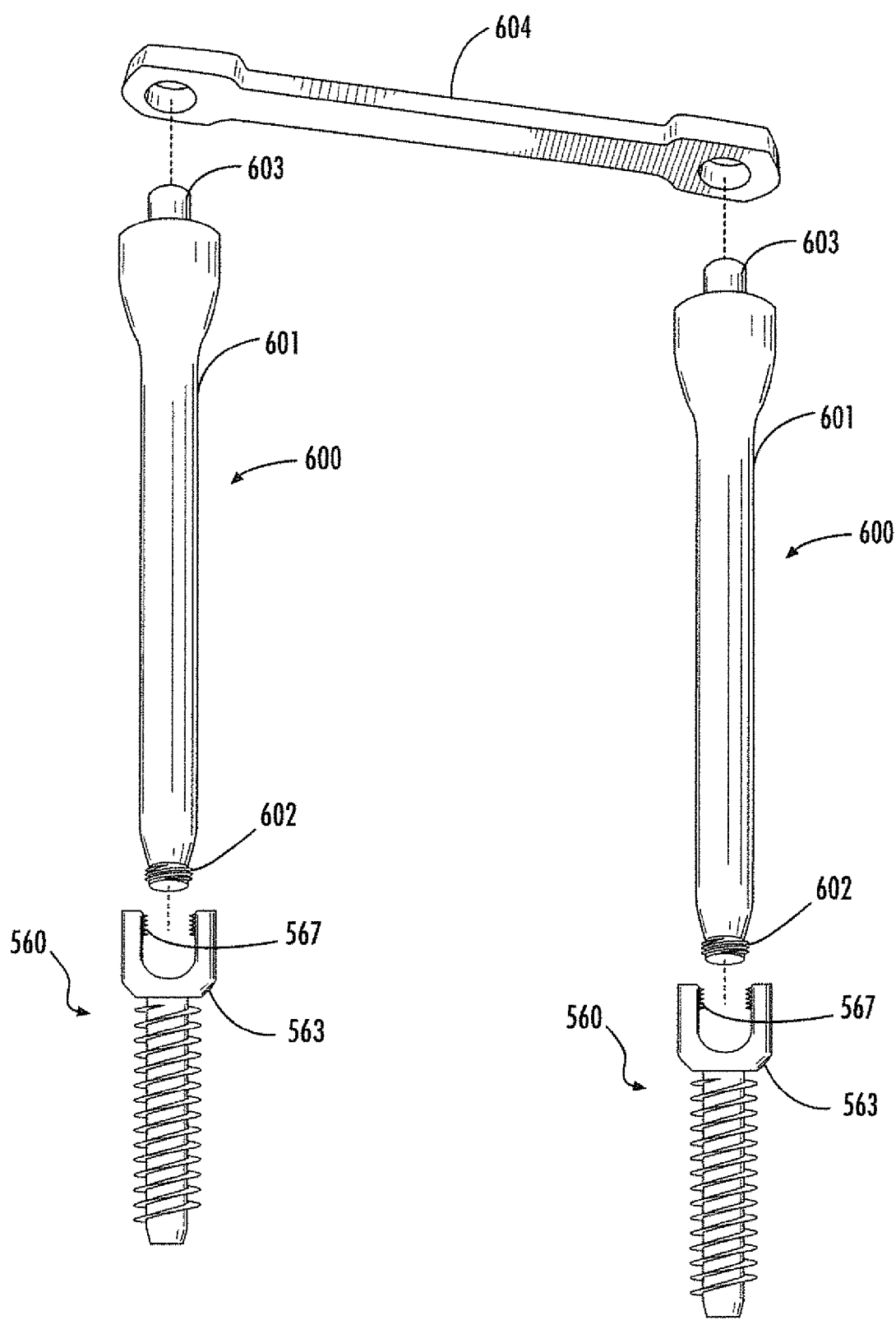
FIG. 13 is a side view of an alignment guide system for use in performing one or more of the methods of FIGS. 1-3.

More particularly, the polyaxial head 89 may advantageously be attached to various pedicle screw heads, directly functioning as a set screw to continue to hold the lumbar rod 95 in place, but with the polyaxial head allowing for relatively easy connection to the support member 85, which is in turn connected to the appropriate iliac screw. The head 89 may provide an attachment for an alignment guide so that the support member 85 (e.g., a rod) may be relatively easily threaded and then captured with the set screw 86 down the shaft of the alignment guide, as will be discussed further below with reference to FIGS. 12 and 13. The polyaxial head 89 may also be used to relatively easily add on to existing spinal constructs without the necessity of extensive removal of existing hardware. Rather, the previously installed set screw may be removed from the lumbar screw head 83, and replaced with the polyaxial head 89.

Also, it should also be noted that a surgeon may decide to install a polyaxial head 89 pre-emptively when performing a lumbar stabilization operation if a future lumbo-pelvic fusion is anticipated. For example, in a sagittal deformity correction it may be decided not to extend to the pelvis, but in case it becomes necessary later the polyaxial head 89 may be installed during the index operation for use at a later time. If and when it is becomes necessary to extend to the pelvis, a subsequent operation may be performed in a near percutaneous fashion. The above-noted configuration advantageously provides desired movability so that the surgeon can more easily align and connect the support member 85 with the head 89, and potentially help expedite the surgery while achieving reduced trauma.

Figure 9A:
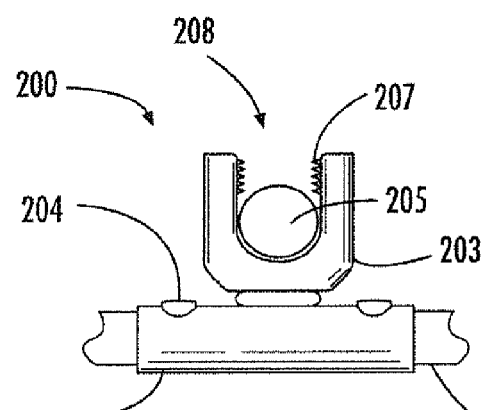
FIGS. 9a and 9b are side and top views, respectively, of a spinal rod connector which may be used with one or more of the methods of FIGS. 1-3.
Figure 9B:
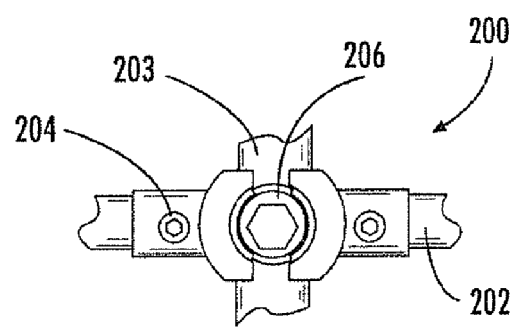

If those cases where there is a previously installed construct 170" (FIG. 16), various attachment devices may be used for attaching or connecting the support member 65" to the existing construct. One such connector 200 is shown in FIGS. 9a and 9b. The connector 200 includes a sleeve 201 which attaches to a lumbar rod 201 (i.e., the lumbar rod passes inside the sleeve) between lumbar pedicle screws to allow for relatively easy connection to the iliac screws. A polyaxial head 203 is carried by the sleeve 201, and since the sleeve may be rotated around the lumbar rod 202 this provides even more flexibility than being mounted on the head of a pedicle screw alone. Here again, the connector 200 may be installed at the time of the spinal operation for immediate pelvic connection, or for easy extension to an iliac support rod 205 at a later date, if desired. One or more set screws 204 may be carried by the sleeve 201 to secure the sleeve to the lumbar rod 202. A set screw 206 may also be used to secure the support rod 205 within a channel 208 of the head 203 via internal threads 207, as seen in FIG. 9b.

Figure 10A:
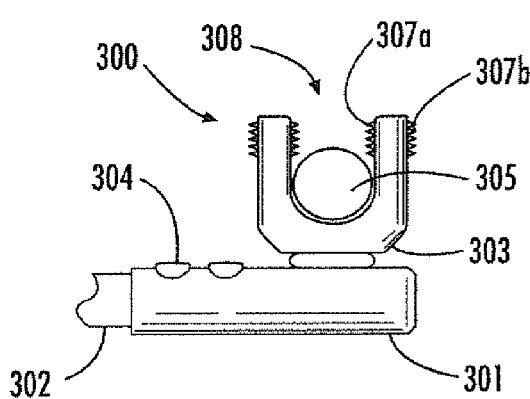
FIGS. 10a and 10b are side and top views, respectively, of a spinal rod end connector which may be used with one or more of the methods of FIGS. 1-3.
Figure 10B:
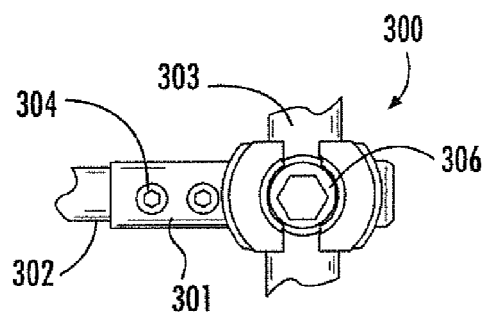

Another example connector 300 is now described with reference to FIGS. 10a and 10b. The connector 300 is configured for attachment to the end of a pre-existing or previously installed construct, e.g., the end of a lumbar rod 302. The connector 300 allows for attachment to the end of a prominent rod 302, or after removal of the most distal or proximal pedicle screw in the construct (e.g., this may be done by removing the last few set screws in the construct and lifting the lumbar rod out of most distal screw head and removing that distal screw). The connector 300 similarly includes a sleeve 301 which fits on the end of the lumbar rod 302, and a polyaxial head 303 is carried by the sleeve. Set screws 304 may be used to secure the sleeve 301 to the lumbar rod 302, and a set screw 306 may be used to secure an iliac support rod 305 to the head 303 via internal threads 307a. In the illustrated configuration, the head 303 has a channel 308 for the iliac support rod 305, and also has external threads 307b on the outside thereof, which may be used for attachment of a guide, etc., in some embodiments, although the external threads need not be included in all embodiments. The external threads 307b may be reversed with respect to the internal threads 307a, for example.

Figure 11A:
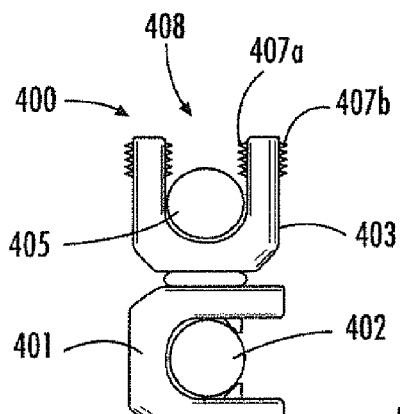
FIGS. 11a and 11b are side and top views, respectively, of a spinal rod side-loading connector which may be used with one or more of the methods of FIGS. 1-3.
Figure 11B:
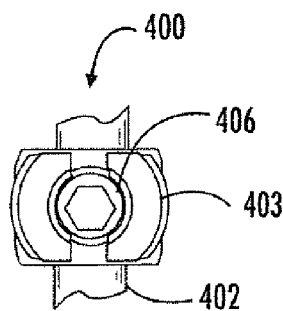

Yet another example connector 400 is now described with reference to FIGS. 11a and 11b. The connector 400 includes a bottom bracket 401 which is configured to attach directly to a lumbar rod 402 of a pre-existing or previously installed construct in a side-loading manner, as seen in FIG. 11a. More particularly, the bottom bracket 401 has a "C" shape that may be placed on the lumbar rod 402 from the side, as shown. The bracket 401 may come in different sizes to accommodate different commercially available rod diameters. A polyaxial head 403 is carried on the bottom bracket 401, and the head has inner threads 407a and outer threads 407b as well as a channel 408. Here again, a set screw 406 may secure an iliac support rod 405 to the head 403 via the inner threads 407a, for example. The connector 400 may be desirable when the pre-existing hardware is difficult to remove or not familiar to the surgeon, for example. In the example of FIG. 16, a similar connector 175" is used which is generally rectangular in shape and has a first channel for receiving the lumbar rod, and a second channel for receiving the iliac rod, as shown, although the illustrated example is not side-loading.

Whether a polyaxial connector on an existing spinal construct or the pedicle screw itself is used, a drill guide 500 (FIG. 12) and/or alignment guides 600 (FIG. 13) may be attached to an iliac screw 560 (and/or pedicle screw) to achieve the proper trajectory and alignment. The drill guide 500 illustratively includes a shaft 501 with a threaded tip 502 to be screwed into the inner threads 567 of the polyaxial head 563 of the iliac screw 560. In particular, the threaded tip 502 may be configured to thread into the inner threads 567 of the head 563 just deep enough to attach thereto, but not deep enough to impede the drill or rod access through the channel of the head. The drill guide 500 further illustratively includes a swing arm 503 having a proximal end rotatably mounted or connected adjacent the top of the shaft 501, and a drill sleeve 504 is connected to a distal end of the swing arm. The drill sleeve 504 may be configured to receive a trocar 505, for example. The drill guide 500 may be connected to a target screw or head with a calibrated alignment guide connector to provide proper trajectory. A head 506 at the top of the shaft 501 may be used for attaching a tool (hex bit, etc.) for screwing and unscrewing the threaded tip 502 with the internal threads 567.

The drill guide 500 with the trocar 505 in place is brought down to the skin overlying the outer table 108' or 109' of the respective ilium 102' or 103'. A small "poke" incision may be made, and the sleeve 501 and tracer 504 are brought down to the given outer table 108' or 109' by the swing arm 503. The trocar 504 may be removed, and a flexible drill may be used to drill across the inner and outer tables 106'/108' or 107'/109' of the crest through the sleeve 504. The support member 65', 65", or 65''' (e.g., rod) is guided percutaneously and connected between the lumbar spine 100' and the respective ilium 102' or 103'. A high speed burr may also be used to burr through the inner/outer tables 106'/108' or 107'/109' under direct visualization once the desired trajectory is set. More particularly, either the drill/guide or high speed burr may be used to remove part of the inner and outer tables 106'/108' or 107'/109' to allow percutaneous passage of the support member 65' (e.g., rod) between iliac screws 506, or to a lumbar screw or construct. Set screws may be applied so that the completed construct is solidly connected, as discussed above.

The alignment guides 600 similarly include shafts 601 with threaded tips 602 which may be threadably connected to the inner threads 567 of the iliac screw heads 563. Heads 603 on the opposing ends of the shafts 601 from the threaded tips 602 are configured for connection to a guide attachment 604. This is advantageous in that the iliac screw heads 563 may be carefully aligned before any bone removal is performed or any support member connected therebetween, which also helps make connecting the support member easier. The guide attachment 604 may be pre-measured in some embodiments so that it is firmly attached or held in place when the shafts 601 are at the proper spacing and angles. Moreover, the guide attachment 604 may also provide the appropriate length to select or cut the support member (e.g., rod) before it is inserted in the patient. The guide attachment 604 may be rigid or semi-rigid, and may be made out of a metal, elastomer, plastic, etc.

In some embodiments the drill guide 500 (i.e., including the swing arm 503 and sleeve 504) may be used in place of one of more of the alignment guides 600. Moreover, when the alignment guide 600 is used with a lumbar or pedicle screw or polyaxial connector head therefor, the threaded tip 602 may be configured to connect to outside or exterior threads (not shown) on an exterior surface of the screw or screw head in some embodiments. This allows a set screw to be passed down through the guide (i.e., through the hollow shaft 601) and attached accordingly. More particularly, the outer threads may be reversed with respect to the inner threads so the shaft 501 or the shaft 601 may be attached. The alignment guide 600 to be used for with iliac screws 560 may be configured to attach to the inner threads 567, because the heads 563 may be buried in the iliac crest, as noted above, although outer threads may be used in some embodiments, if desired.

Figure 2:
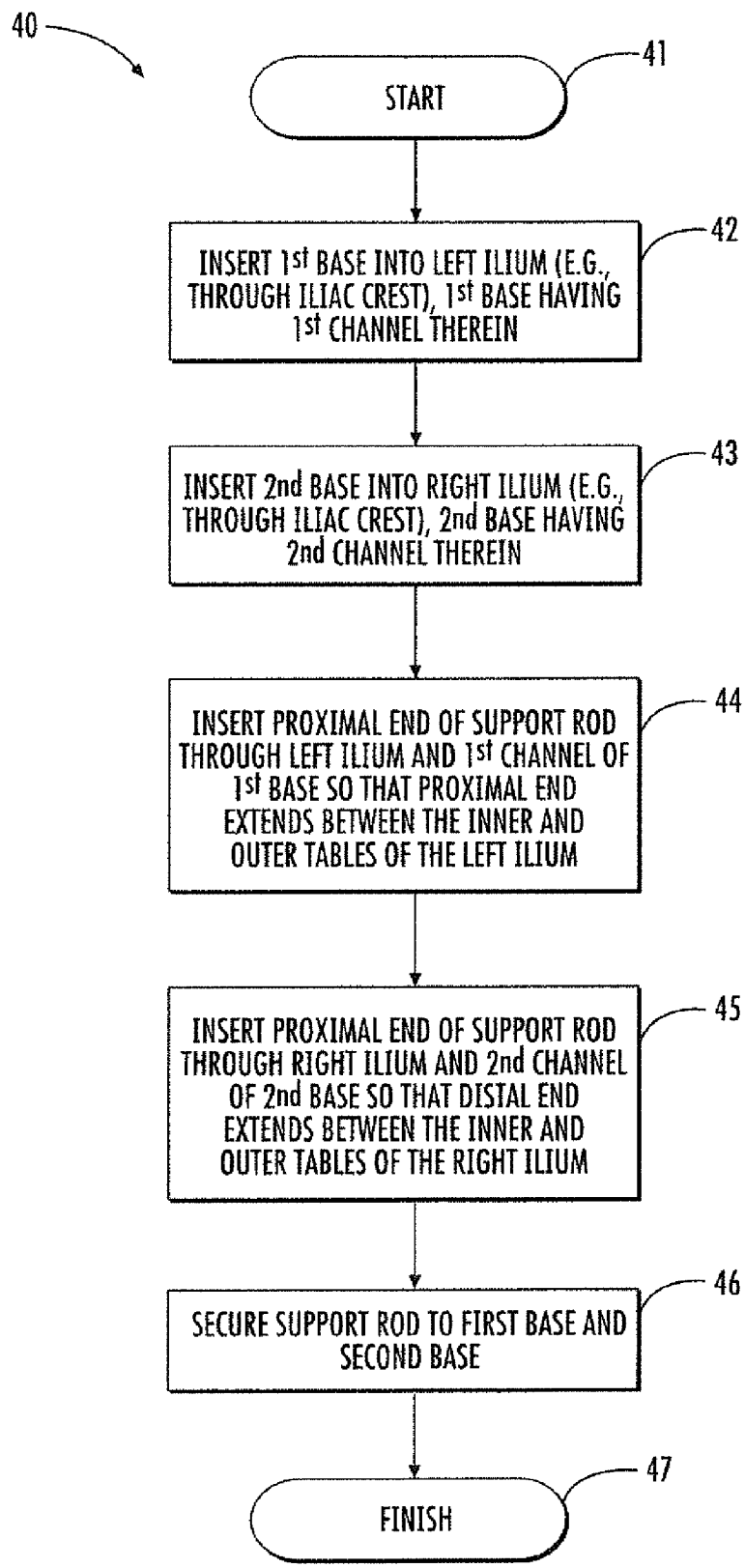

Referring to FIG. 14 and also the flow diagram 40 of FIG. 2, with respect to a trans-iliac stabilization procedure the same technique for iliac crest exposure as described above is used, except that a more distal portion of the iliac crests 104, 105 may be chosen as a starting point. That is, the screws 60 may be inserted in a more distal location toward the back of the iliac crests 104, 105, as can be seen in FIG. 17 where separate sets of iliac screws have been inserted in the respective iliac crests for both the trans-iliac stabilization and the lumbo-pelvic stabilization. The screws 60 and heads 63 may also be applied in a similar manner as well. Beginning at Block 41, after the screws 60 are inserted, at Blocks 42-43, either a trans-iliac drill and guide or a high speed burr may be used to remove the appropriate bone for placement of the trans-iliac support member 65 (e.g., rod). The proximal and distal ends of the rod may then be guided between the two screw heads 63 and iliac crest via a small stab incision, at Blocks 44-45. After appropriate compression, the set screws 66 are applied to secure the rod in place, at Block 46, which concludes the illustrated method. This advantageously provides desired multidirectional stability across the SI joints and sacrum whereas traditional ilio-sacral lag screws may not. The trans-iliac rod 65 may accordingly be used to provide trans-iliac fixation to allow for controlled compression across damaged/displaced SI joints, for example.

As seen in FIGS. 14 and 17, the trans-iliac fixation may be used alone or in combination with a lumbo-pelvic construct, as discussed above. Moreover, if SI joint fusion is desired, it may be achieved through the same small incision used to apply the iliac screw, just by centering the incision slightly medial. The amount of soft tissue dissection is relatively small, but a relatively high degree of stability is provided by the completed construct. It should also be noted that, in some embodiments, a trans-iliac fixation may be used as an anchor or connection point. That is, similar to the way the lumbar rod may be used as an anchor point for the lumbo-pelvic rod, a trans-iliac rod (or other support member) may similarly be used as an anchor point for a different lumbar or pelvic construct, for example.

Accordingly, various features and advantages may become apparent to the skilled artisan in view of the above description. Since the iliac screw may be buried in the ilium and recessed below the surface of the iliac crest, with the stabilization member or rod being passed through the ilium between the inner and outer tables, this may provide for reduced hardware prominence and accordingly a reduced likelihood of pressure soreness to the patient after surgery. Use of the alignment guides may advantageously allow the desired trajectory to be planned before any bone is removed or rod is inserted. The use of polyaxial connectors may allow for easier alignment and connection of the support rods, and these connectors may also be used in supplemental thoracolumbar surgery, if desired. As a result of these advantages, the above-described approaches and devices may allow for relatively shorter surgical times and trauma to the patient.

By way of contrast, typical fixation systems are installed with the iliac screws sticking out of (i.e., protruding outwardly from) the iliac crest, and then being attached to the lumbar spine construct in a relatively cumbersome and destructive large open incision. However, the above-described approach may advantageously utilize a small incision centered over the posterior iliac crest/SI joint area, and a guide system to drill through the iliac crest and pass the rod through the screw and iliac crest either to the lumbar construct or to the other iliac crest without direct dissection. This makes the process faster and less destructive to the patient's tissue.

The above-described trans-iliac fixation approach may advantageously be used to treat unstable pelvic/SI joint injuries and standalone SI joint fusion, for example, because it allows compression across the construct. In some embodiments, one or more SI joint cages may be used for the external SI joint anatomy, as the above-describe approach may enable placement of one or more cages across the SI joint to facilitate fusion through bone ingrowth. The above-described approach may also allow relatively easy accommodation to the variable anatomy of the SI joint, and relatively easy access to the SI joint via the same small iliac incision.

By way of example, the iliac stabilization approach described above may be used in a variety of applications, such as a lumbo-pelvic reconstruction, complex spinal deformity, and/or pelvic ring trauma. Pelvic ring trauma is often relatively complex, especially in the light of SI joint disruption and displaced sacral fractures. Particularly difficult are the vertically displaced fractures, which often require lumbo-pelvic stabilization or stronger bilateral SI joint stabilization than typical percutaneous sacro-iliac fixation, which provides poor rotational and vertical control in these injuries. Typical systems that are designed to connect the pelvis to the lumbar spine are relatively bulky and require extensive dissection to put in place. Connecting the screws to the rest of the construct may also be time consuming and awkward. Further, typical iliac screws may be bulky, leading to pressure soreness and painful hardware complaints.

The above-noted approach may also be useful to stabilize a patient with multiple injuries, yet without the usual aggressive dissection and increased infection risk. It may also be used in complex spine deformity cases requiring stabilization and/or fusion down to the pelvis, and for patients who develop lumbo-pelvic deformity or sacral fracture after multi-level lumbar fusion. It may also provide an option to add to a preexisting fusion without removing or adjusting the previous hardware, as noted above.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A surgical method for at least one ilium having opposing inner and outer tables and an iliac crest defining a ridge at the top of the ilium between the inner and outer tables, the method comprising:
   inserting at least one base into the ilium penetrating the ridge of the iliac crest from a posterior position at a downward angle, the at least one base having a channel therein;
   inserting a support member through the ilium and through the channel of the at least one base so that the support member extends between the inner and outer tables; and
   securing the support member to the at least one base.

2. The method of claim 1 wherein the support member comprises a rod.

3. The method of claim 1 wherein the at least one ilium comprises a left ilium and a right ilium;
   wherein inserting the at least one base comprises inserting a first base in the left ilium and a second base in the right ilium;
   wherein inserting the support member comprises inserting a proximal end of a support member through the left ilium and the first channel of the first base so that the proximal end extends between the inner and outer tables of the left ilium, and inserting a distal end of the support member through the right ilium and the second channel of the second base so that the distal end extends between the inner and outer tables of the right ilium; and
   wherein securing comprises securing the support member to the first base and the second base.

4. The method of claim 1 wherein inserting the support member comprises inserting a proximal end of the support member through the ilium and through the channel of the at least one base; and further comprising coupling a distal end of the support member to an adjacent vertebral body.

5. The method of claim 4 wherein coupling the distal end of the support member to the adjacent vertebral body comprises coupling the distal end to a bone screw device carried by the adjacent vertebral body.

6. The method of claim 5 wherein the bone screw device comprises
a threaded base configured to be screwed into the vertebral body,
a first head carried by the threaded based and defining a first channel therein, the first channel configured to receive a support rod, and the first head having first internal threads within the first channel, and
a second head comprising a threaded base configured to be threadably coupled with the first inner threads to secure the support rod within the first channel of the first screw head, and an articulating head portion coupled to the threaded base and defining a second channel therein, the articulating head configured for polyaxial movement relative to the threaded base;
and wherein coupling the distal end of the support member to the adjacent vertebral body comprises coupling the distal end of the support member within the second channel of the articulating head portion.

7. The method of claim 4 wherein coupling the distal end of the support member to the adjacent vertebral body comprises coupling the distal end to a spinal rod also coupled to the adjacent vertebral body.

8. The method of claim 1 wherein the at least one base has a threaded exterior; and wherein inserting the at least one base into the ilium comprises screwing the at least one base into the ilium through the iliac crest.

9. The method of claim 1 wherein inserting the base into the ilium further comprises recessing the base within the ilium so that the base is flush with or below a surface of the iliac crest.

10. The method of claim 1 wherein the at least one base comprises an articulating head defining the channel therein.

11. The method of claim 10 wherein the articulating head has a threaded interior; and wherein securing the support member further comprises threadably fastening a set screw to the interior threads of the articulating head.

12. The method of claim 1 further comprising coupling a guide member to the at least one base for aligning the support member.

13. A surgical method for connecting a support rod between a left ilium and a right ilium, the left ilium and the right ilium each having respective inner and outer tables and an iliac crest defining a ridge at the top of the ilium between the inner and outer tables, the method comprising:
inserting a first base into the left ilium and penetrating the ridge of the iliac crest thereof from a posterior position at a downward angle, the first base having a first channel therein;
inserting a second base into the right ilium and penetrating the ridge of the iliac crest thereof from a posterior position at a downward angle, the second base having a second channel therein;
inserting a proximal end of a support rod through the left ilium and the first channel of the first base so that the proximal end extends between the inner and outer tables of the left ilium;
inserting a distal end of the support rod through the right ilium and the second channel of the second base so that the distal end extends between the inner and outer tables of the right ilium; and
securing the support rod to the first base and the second base.

14. The method of claim 13 wherein the first base and the second base each has a threaded exterior; wherein inserting the first base comprises screwing the first base into the left ilium through the iliac crest thereof; and wherein inserting the second base comprises screwing the second base into the right ilium through the iliac crest thereof.

15. The method of claim 13 wherein inserting the first base into the left ilium further comprises recessing the first base within the left ilium so that the first base is flush with or below a surface of the iliac crest thereof; and wherein inserting the second base into the right ilium further comprises recessing the second base within the right ilium so that the second base is flush with or below a surface of the iliac crest thereof.

16. A surgical method for connecting a support rod between an ilium having opposing inner and outer tables and an iliac crest defining a ridge at the top of the ilium between the inner and outer tables, and an adjacent vertebral body, the method comprising:
inserting a base into the ilium penetrating the ridge of the iliac crest from a posterior position at a downward angle, the base having a channel therein;
inserting a proximal end of the support rod through the ilium and through the channel of the base so that the support rod extends between the inner and outer tables;
connecting a distal end of the support rod to the adjacent vertebral body; and
securing the support rod to the base.

17. The method of claim 16 wherein connecting the distal end of the support rod to the adjacent vertebral body comprises connecting the distal end to a bone screw carried by the adjacent vertebral body.

18. The method of claim 16 wherein connecting the distal end of the support rod to the adjacent vertebral body comprises connecting the distal end to an inter-vertebral rod also connected to the adjacent vertebral body.

19. The method of claim 16 wherein the base has a threaded exterior; and wherein inserting the base into the ilium comprises screwing the base into the ilium through the iliac crest.

20. The method of claim 16 wherein inserting the base into the ilium further comprises recessing the base within the ilium so that the base is flush with or below a surface of the iliac crest.

* * * * *